(12) United States Patent
McNestry et al.

(10) Patent No.: US 9,145,021 B2
(45) Date of Patent: Sep. 29, 2015

(54) SYSTEM FOR MEASURING RIBBON TENSION

(75) Inventors: Martin McNestry, Heanor (GB); Gary Pfeffer, Woodthorpe (GB)

(73) Assignee: Videojet Technologies Inc., Wood Dale, IL (US)

( * ) Notice: Subject to any disclaimer, the term of this patent is extended or adjusted under 35 U.S.C. 154(b) by 40 days.

(21) Appl. No.: 13/979,763

(22) PCT Filed: Jan. 17, 2012

(86) PCT No.: PCT/US2012/021522
§ 371 (c)(1),
(2), (4) Date: Jul. 15, 2013

(87) PCT Pub. No.: WO2012/099862
PCT Pub. Date: Jul. 26, 2012

(65) Prior Publication Data
US 2013/0286138 A1    Oct. 31, 2013

Related U.S. Application Data

(60) Provisional application No. 61/434,599, filed on Jan. 20, 2011.

(51) Int. Cl.
| | | |
|---|---|---|
| *B41J 31/00* | (2006.01) | |
| *B41J 35/08* | (2006.01) | |
| *B41J 2/325* | (2006.01) | |
| *G01L 5/10* | (2006.01) | |
| *B41J 31/05* | (2006.01) | |
| *G01N 3/00* | (2006.01) | |
| *B41J 35/36* | (2006.01) | |
| *B41J 31/04* | (2006.01) | |

(52) U.S. Cl.
CPC ...... *B41J 35/08* (2013.01); *B41J 2/325* (2013.01); *B41J 31/04* (2013.01); *B41J 31/05* (2013.01); *B41J 35/36* (2013.01); *G01L 5/10* (2013.01); *G01N 3/00* (2013.01)

(58) Field of Classification Search
USPC ......... 347/211, 213–215, 217–219, 222, 171, 347/173, 175, 176, 101, 104, 16; 400/611, 400/613, 618, 621, 621.1, 120.02–120.04, 400/218, 234, 223, 239
See application file for complete search history.

(56) References Cited

U.S. PATENT DOCUMENTS

| | | | | |
|---|---|---|---|---|
| 4,517,573 | A | * | 5/1985 | Yana .............................. 347/217 |
| 5,636,331 | A | * | 6/1997 | Klinefelter et al. ........... 347/193 |
| 5,853,255 | A | | 12/1998 | Soshi et al. |
| 6,130,699 | A | | 10/2000 | Christensen et al. |
| 6,412,991 | B1 | | 7/2002 | Klinefelter et al. |
| 7,089,420 | B1 | | 8/2006 | Durst et al. |
| 7,150,572 | B2 | | 12/2006 | McNestry |
| 7,773,749 | B1 | | 8/2010 | Durst et al. |
| 7,995,196 | B1 | | 8/2011 | Fraser |
| 2011/0074905 | A1 | * | 3/2011 | Marcus et al. ................ 347/218 |

* cited by examiner

*Primary Examiner* — Kristal Feggins
(74) *Attorney, Agent, or Firm* — Joseph A. Yosick

(57) ABSTRACT

A ribbon includes a substrate film, wherein the film comprises a tensionable material; and an ink disposed on the ribbon. A length of the ribbon includes portions that have been tensioned to provide a code readable from the ribbon by measuring the tension over the length of the ribbon.

13 Claims, 6 Drawing Sheets

SYSTEM FOR MEASURING RIBBON TENSION

RELATED APPLICATIONS

This application claims priority under 35 U.S.C. §371 from PCT Application No. PCT/US2012/021522, filed in English on Jan. 17, 2012, which claims the benefit of U.S. Provisional Application No. 61/434,599 filed Jan. 20, 2011, the disclosures of both of which are incorporated herein be reference in their entireties.

BACKGROUND

The present disclosure relates to a method of reading a code from a ribbon for a printer. In particular, the disclosure relates to a method of identifying the properties of a ribbon for a printer by measuring the tension of the ribbon.

There are many types of devices that use ribbon, including various types of printers such as thermal transfer printers. The ribbons may be of various types, including different widths, lengths, thicknesses, ink colors, ribbon materials, and so forth. Typically, the ribbons are supplied on simple spools (which may be, for example, a cardboard tube). Thus, the ribbon itself does not provide to the printer any information on the qualities of the ribbon; instead, it is up to the user to select the proper ribbon type and operate the printer accordingly.

BRIEF SUMMARY

The present disclosure provides a method for identifying properties of a ribbon by imparting specific tension features and then measuring those features to provide a code. The code provides information about the ribbon, allowing the printer to automatically detect certain properties of the ribbon by measuring the tension along a portion of the ribbon.

In one aspect, a ribbon includes a substrate film, wherein the film comprises a tensionable material, and an ink disposed on the film. A length of the ribbon includes portions that have been tensioned to provide a code readable from the ribbon by measuring the tension over the length of the ribbon.

In another aspect, a method for reading a code from a ribbon for a printer includes providing a printer and providing a ribbon. The ribbon is encoded with data. The ribbon is inserted into the printer. The ribbon is run through a portion of the printer. A parameter indicative of tension in the ribbon is measured to provide tension data. An algorithm is performed on the tension data to read a code. At least one feature of the printer is operated based on the code.

In another aspect, a method of imparting a tension code on a ribbon includes providing a ribbon and a spool. The ribbon is wound onto the spool. While winding the ribbon onto the spool, a force applied to the ribbon is varied to impart a tension code on the ribbon.

The foregoing paragraphs have been provided by way of general introduction, and are not intended to limit the scope of the following claims. The presently preferred embodiments, together with further advantages, will be best understood by reference to the following detailed description taken in conjunction with the accompanying drawings.

DETAILED DESCRIPTION

Figure 1:
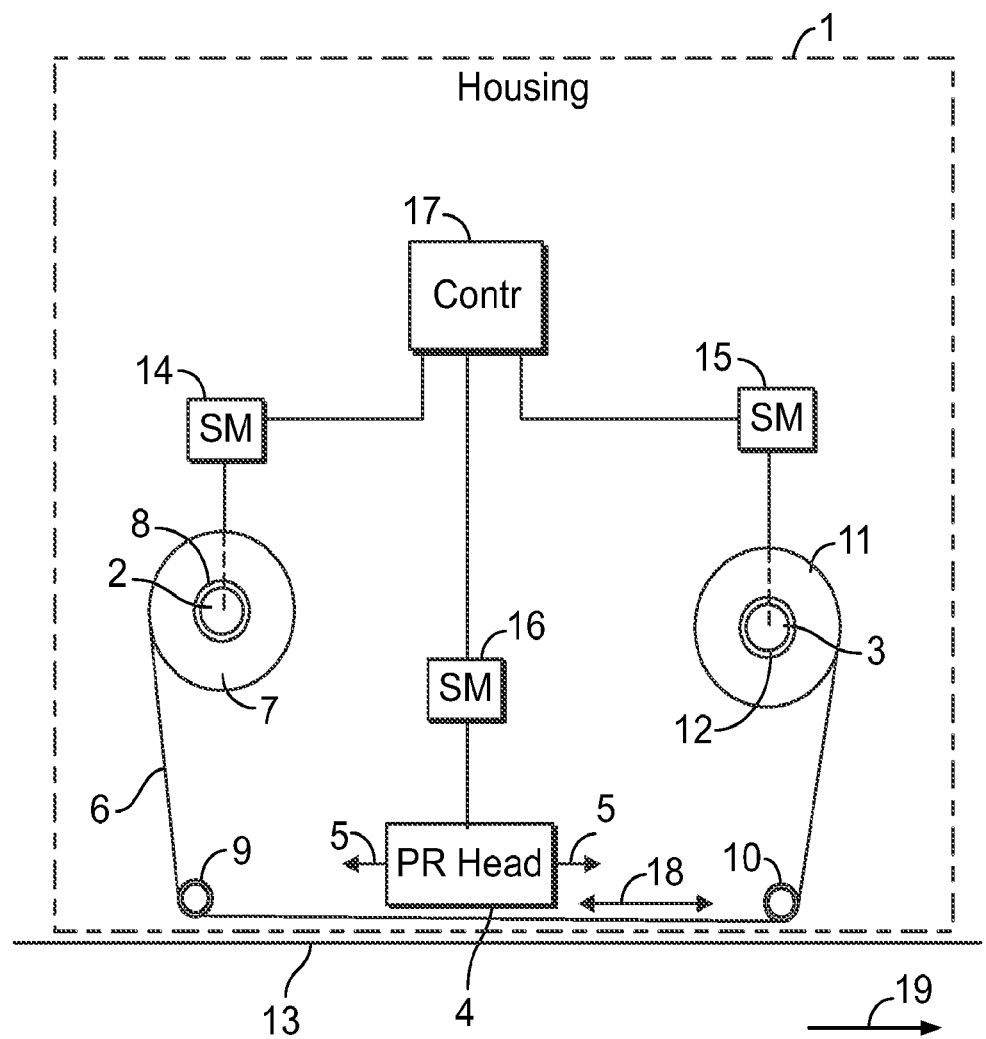
FIG. 1 shows an embodiment of a printer and a ribbon.

The invention is described with reference to the drawings in which like elements are referred to by like numerals. The relationship and functioning of the various elements of this invention are better understood by the following detailed description. However, the embodiments of this invention as described below are by way of example only, and the invention is not limited to the embodiments illustrated in the drawings.

The present disclosure provides a system that allows information to be encoded in a ribbon in the form of variations in the tension of a wound ribbon which may then be read during printing to extract a code. The code enables the automatic configuration of the printing system for parameters such as ribbon width, length or color. The system is particularly suitable for use with thermal transfer printers, particularly thermal transfer overprinters (TTO). However, the system is suitable for any type of device that uses a ribbon that is capable of being tensioned, including, for example, impact printers.

The ribbon used with the system may be a conventional ribbon for a TTO printer. The ribbon includes a substrate film and an ink disposed on the film. The ink may be, for example, a liquid ink or a solid ink that is melted by the heating elements of a print head. The film includes a tensionable material. By "tensionable" is meant that a change may be made to the ribbon that can later be identified by measuring the tension in the ribbon. In particular, portions of the ribbon are tensioned differently such that a code is readable from the ribbon by measuring the tension over those portions of the ribbon. The ribbon may be tensioned (i.e. modified to produce portions with different measurable tension) by any suitable method. For example, the ribbon may be tensioned by pulling on discrete portions of the ribbon as it is wound onto the spool. Alternatively, the tension may be imparted by varying the torque or speed on the winding spool to produce the tension code. The ribbon could also be tensioned by controlling the structure of the ribbon or its substrate film during the manufacture of the ribbon (such as providing different thicknesses, densities, or other material properties) to provide the desired tensioned portions. The tensioned code is preferably imparted to the ribbon during production while the ribbon is wound onto a spool. The ribbon is typically between 5 and 10 microns thick and from 100 to 1500 meters in length.

The code is provided in the material by providing areas or portions of different tension along a length of the ribbon. The code is preferably a binary code and is preferably at least a 4 bit code. Alternatively, the code may be an analog code. The length of the ribbon that includes portions that have been tensioned with code may include a length of ribbon equivalent to two circumferences of a spool, which in one embodiment may be at least 2 m.

The code is identified by measuring the tension in the ribbon as it is un-wound from the spool, typically after the ribbon is inserted into a printer. The tension may be measured by any suitable method. The tension may be calculated from measures of power supplied to the two motors, measures of the spool radii, and calibration factors for the two motors related to the step rate of the motors. Alternatively, the tension may be measured directly, such as with a load cell contacting the ribbon, or a movable roller, movement of which is resisted by a progressive spring and the position of which is measured by one or more position sensors.

In one embodiment, a system for measuring the tension of a ribbon includes a ribbon, a drive mechanism for the ribbon, and a tension detector. An embodiment of such a system is found in U.S. Pat. No. 7,150,572 (the contents of which are hereby incorporated by reference) and is shown in FIG. 1. Referring to FIG. 1, the schematically illustrated printer in accordance with an exemplary embodiment has a housing represented by broken line 1 supporting a first shaft 2 and a second shaft 3. A displaceable print head 4 (PR Head) may be mounted on the housing, the print head 4 being displaceable along a linear track as indicated by arrows 5. A printer ribbon 6 extends from a spool 7 received on a spool support 8 which is driven by the shaft 2 around rollers 9 and 10 to a second spool 11 supported on a spool support 12 which is driven by the shaft 3. The path followed by the ribbon 6 between the rollers 9 and 10 passes in front of the print head 4. A substrate 13 upon which print is to be deposited follows a parallel path to the ribbon 6 between rollers 9 and 10, the ribbon 6 being interposed between the print head 4 and the substrate 13.

The shaft 2 is driven by a stepper motor 14 (SM) and the shaft 3 is driven by a stepper motor 15 (SM). A further stepper motor 16 (SM) controls the position on its linear track of the print head 4. A controller 17 (Contr) controls each of the three stepper motors 14, 15 and 16 as described in greater detail below, the stepper motors being capable of driving the print ribbon 6 in both directions as indicated by arrow 18. Although FIG. 1 shows a particular embodiment of a printer that may use the verification system described herein, it is to be understood that this is just an exemplary embodiment and the verification system may be used with other types of printers and devices.

The present disclosure further provides a method of verifying a ribbon for a printer. The encoded ribbon is inserted into the printer and run through a portion of the printer. For example, the ribbon may be provided on a spool, which is disposed on a first spool support of the printer, with an end of the ribbon being wound on another spool disposed on a second spool support of the printer. A parameter indicative of the tension in the ribbon, or the tension of the ribbon itself, is measured to provide tension data. An algorithm is performed on the tension data to read a code. For example, the code may include information about the length, width, thickness, color, or ink type of the ribbon. At least one feature of the printer is operated based on the code. Thus, the operating parameters of the printer may depend on the code. Such operating parameters may include the maximum print speed, the nominal tension setting, and the heating parameters for the print head.

The algorithm may include a variety of steps or data transformations to obtain the code. In particular, the data may be corrected based on the operation of the printer. The data may also be filtered to remove noise. Mathematical operations may be performed on the data, such as taking the derivative of the data.

If a digital code is used, the code is preferably a sufficient number of bits to ensure that the desired information is accurately and reliably provided to the printer. The code may range from four to ten or more bits. In one embodiment, the code is at least four bits. The code may include two portions, a start sequence and a data sequence. One or more bits of the data sequence may be used to provide parity for error detection. Although longer codes increase the amount of data which can be encoded, they also will cause the data acquisition time of the system to increase.

The code imparted on the ribbon provides modulation of the tension in the wound ribbon over a length of the ribbon. The process of measuring the tension (or a parameter indicative of tension) over a portion of the ribbon may be repeated one or more times on the ribbon to provide redundancy of the data, and to allow data acquisition when a partially used ribbon is loaded onto a printer. The tension may be measured at least once per revolution. However, more frequent tension measurements are of course possible.

The tension modulation process adds the code to the ribbon tension using pulse coded modulation. A pair of tension levels or thresholds is used to represent each binary digit as either a '0' or a '1'. The optimum values of the thresholds depend on various properties of the ribbon, including width and material of construction, and may be determined empirically by experimentation. In one embodiment, for a 55 mm wide ribbon, the nominal tension during use of the ribbon is 4 Newtons and the actual values used are 0.8 Newton and 2.4 Newton to represent '0' and '1' respectively. As the code is created while winding the ribbon, but read back while unwinding the ribbon, the sequence of the code is preferably reversed when being encoded during the winding process.

In operation of one type of TTO printer (for example, the Videojet DataFlex® Plus), the printer constantly monitors the ribbon tension between the two spools, and makes corrections to the movement of the motors in order to keep the tension within a range suitable for satisfactory printing. However, the present system could be implemented in any printer which is able to measure tension (or measure a parameter indicative of tension to indirectly derive tension from other properties) in the installed ribbon.

Figure 2:
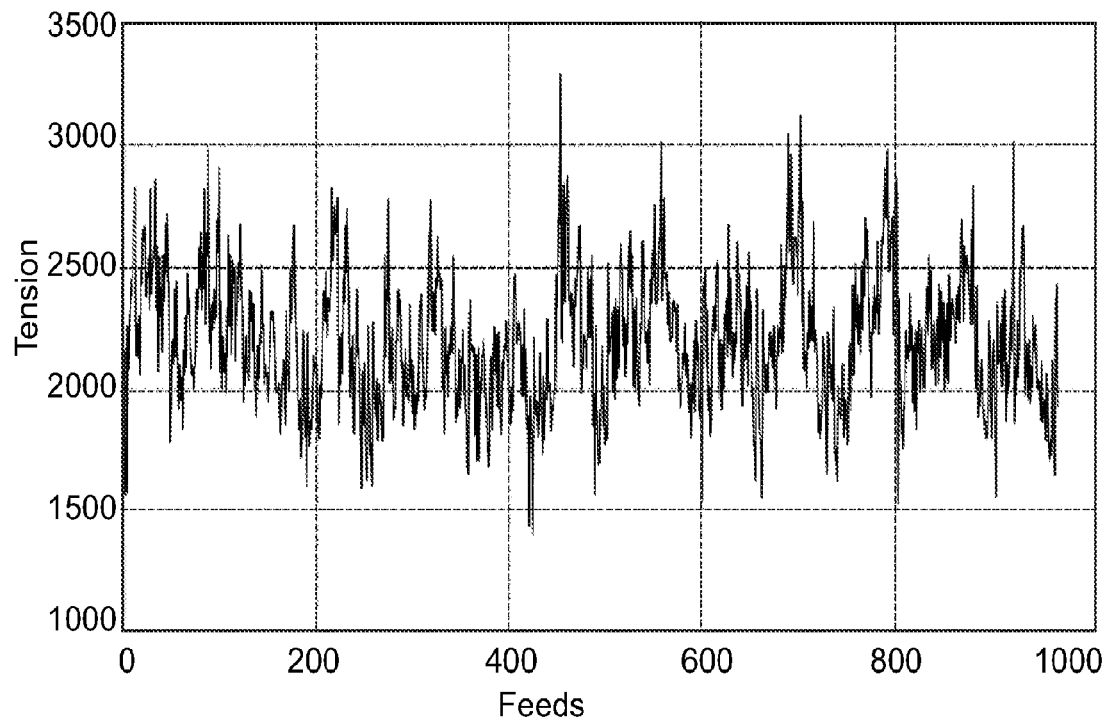
FIG. 2 is a graph showing the raw tension data from an embodiment of a ribbon.
Figure 3:
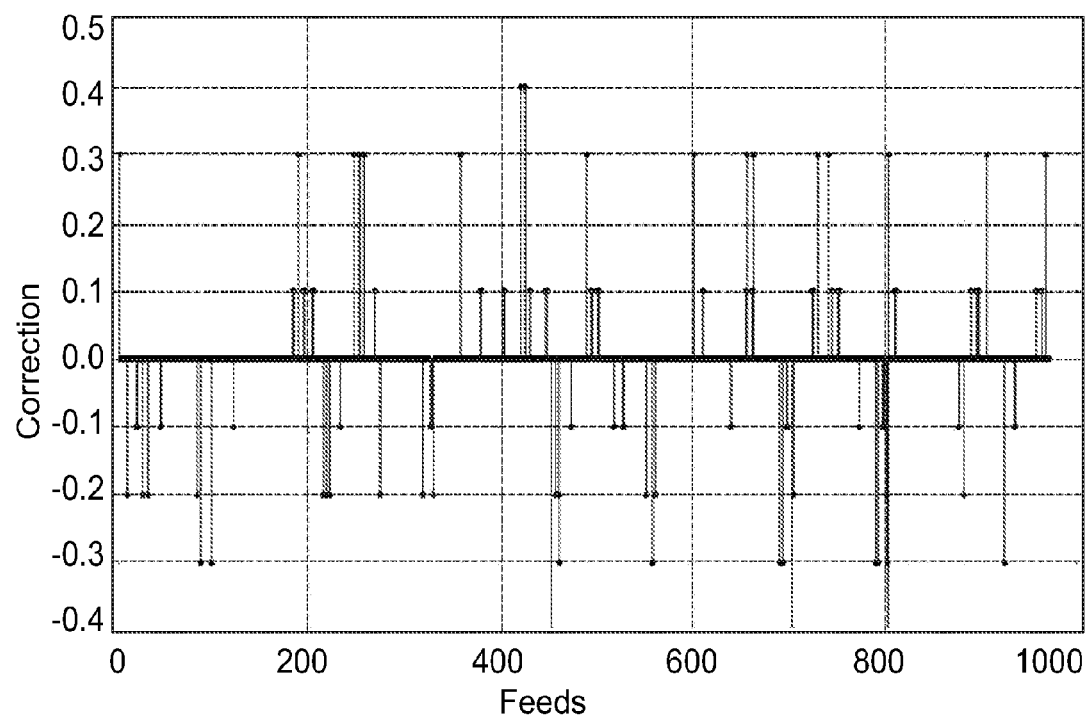
FIG. 3 is a graph showing the corrections applied to the ribbon of FIG. 2.
Figure 4:
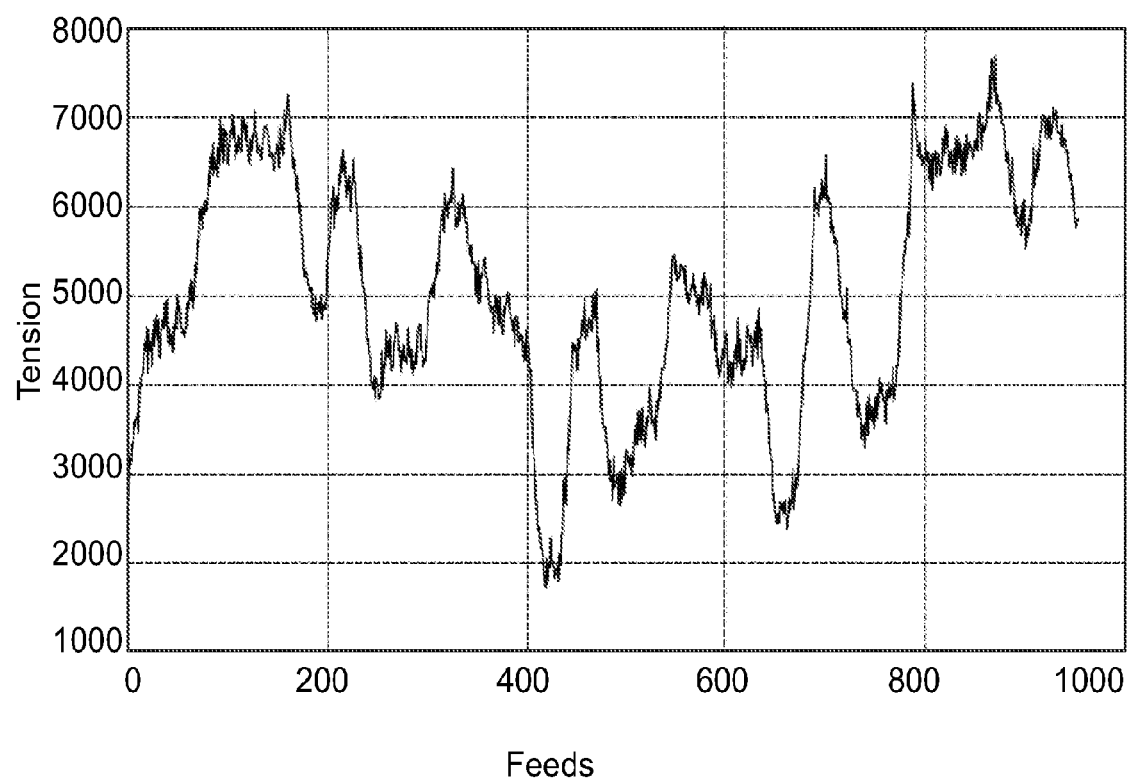
FIG. 4 is a graph showing corrected tension data from an embodiment of a ribbon.

If the ribbon contains a code encoded in the tension of the ribbon as described above, the printer will detect these tension variations and attempt to correct for them. An embodiment of a method of analyzing tension data to provide a code will be described with respect to an example of tension data. FIG. 2 shows an example of a set of tension readings taken during normal operation of a Videojet DataFlex® Plus printer (which includes the mechanism shown in FIG. 1), using a ribbon which has data encoded onto it. The Y axis represents arbitrary units of measured tension and the X axis represents the number of feeds. In order to extract the encoded data, the measured tension is used along with knowledge of any corrections made by the printer to obtain the proper tension, to reconstruct the true tension profile of the ribbon. In particular, each time a correction is made by adding or subtracting a certain amount of ribbon from the system, it is done with the aim of correcting for an amount of excess under- or overtension. The amount of tension which is being corrected for is added to a running tension offset. The 'true' tension at any point is then the sum of the current tension value and the running tension offset. FIG. 3 shows the corrections made by the printer in the tension readings of FIG. 2. The true tension profile represents what the tension would have been if no corrections were applied (and if the resulting tension did not cause the ribbon to break or go slack). FIG. 4 shows the results of this correction process applied to the data used for FIG. 2.

Figure 5:
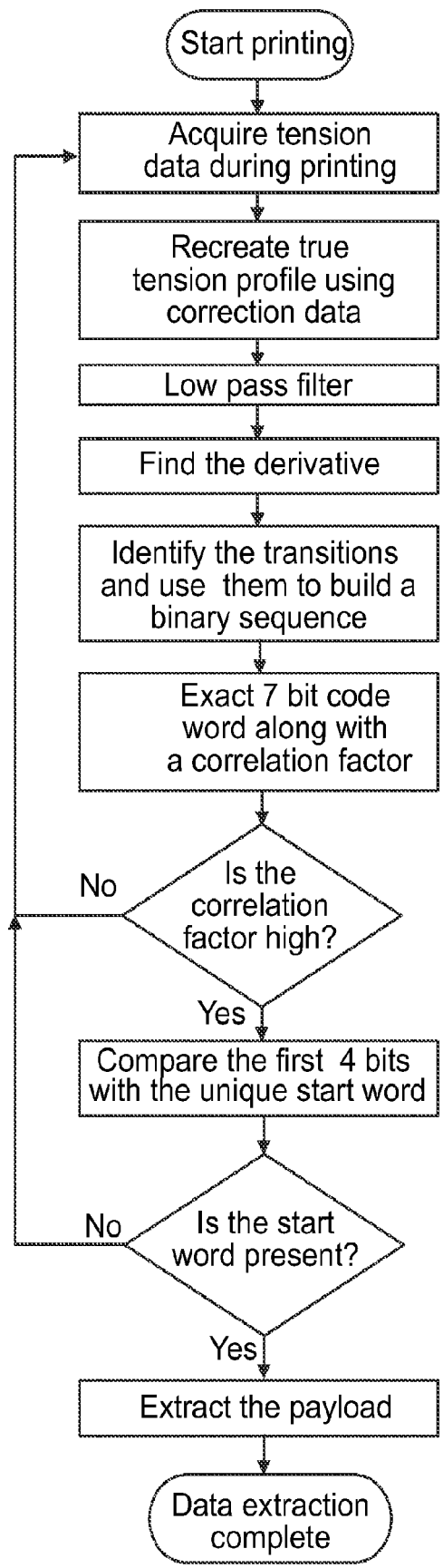
FIG. 5 is a flow chart showing the steps of one embodiment of a ribbon detection process.

After recreating the true tension profile, the data is then passed through a number of signal processing stages, resulting in the extraction of the code. An embodiment of a full process for the extraction of the code is shown in FIG. 5. The process functions as a pipeline and the enumerated steps are executed each time a new item of tension data is generated; normally this occurs at the end of each print feed. The new item of tension data, along with the corresponding item of correction data, is used to calculate the true tension.

Figure 6:
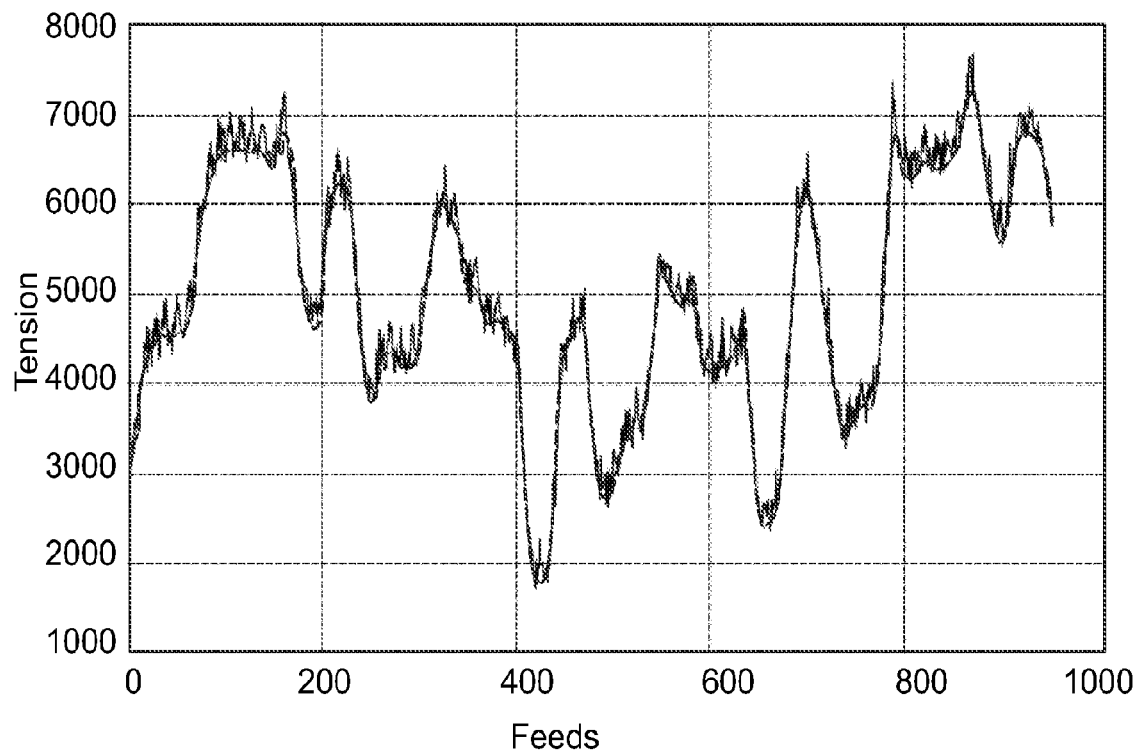
FIG. 6 is a graph showing the tension data of FIG. 3 before and after filtering.

The true tension data is then subjected to a digital low pass filter. Any suitable digital filter may be used. The filter type and properties may depend on the type of printer and ribbon. A preferred filter is a 31-tap FIR filter with a cut-off frequency of 1.3 cycles/meter. However, other low pass filter implementations or cut-off frequencies may used. The key point is that the filter removes noise from the signal, leaving just a slow moving signal in its output. FIG. 6 is a graph showing the tension data of FIG. 3 before and after filtering. The noisy line is the unfiltered signal; the smooth line shows the signal after low-pass filtering.

Figure 7:
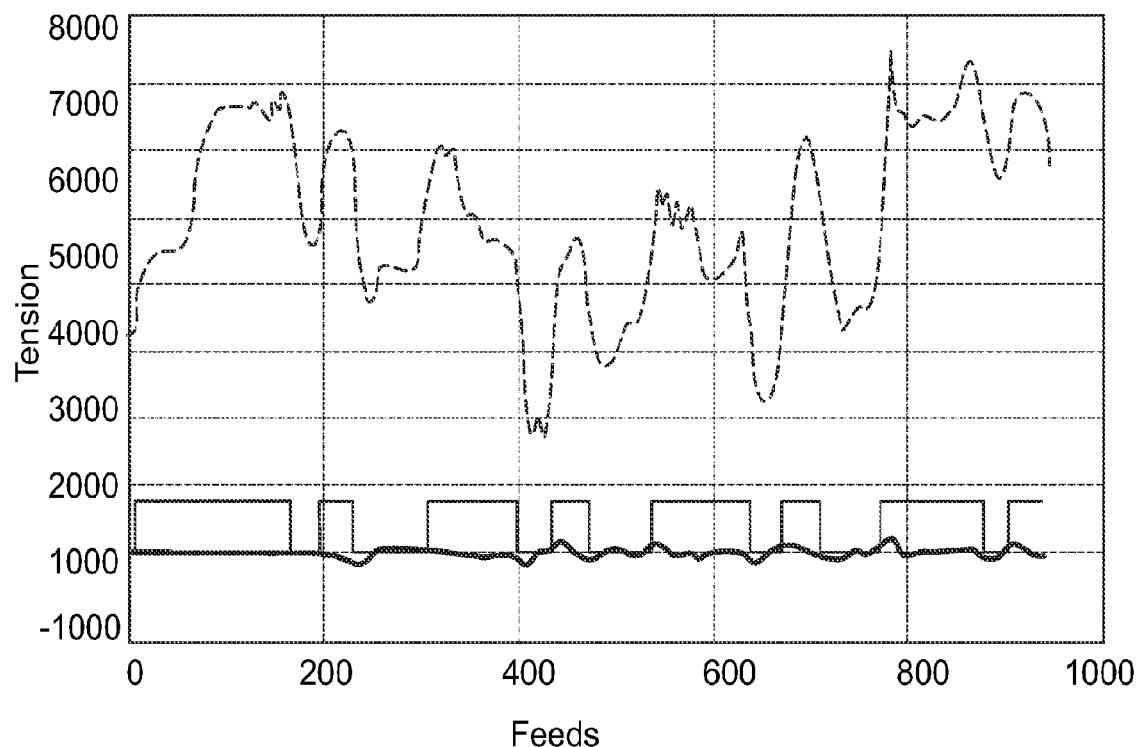
FIG. 7 is a graph showing the filtered data and the derivative of the filtered data of FIG. 6.

Next, the derivative of the filtered signal of FIG. 6 is calculated by taking the difference between each data point and the data point immediately preceding it. Then, positive and negative threshold levels are applied. The use of these thresholds allows transitions to be identified: where the absolute value of the derivative exceeds (i.e. is more positive than) the positive threshold, a low-to-high level transition is occurring. Where the absolute value of the derivative exceeds (i.e. is more negative than) the negative threshold, a high-to-low level transition is occurring. Where there is no transition the previous level is maintained. FIG. 7 illustrates the calculation of transitions based on the thresholds.

Overall, this process transforms the items of tension data into one of two levels, and the data resulting from this is fed into a memory buffer, whose size is equal to that necessary to contain data equivalent to one code.

The next step is to extract the code from the processed signal. In the preferred method, the code is extracted by splitting the processed data into a number of zones equal to the number of bits, wherein each zone corresponds to a bit from the code. In each zone, the area under the curve is measured. The maximum possible area corresponds to that of an ideal '1'. An ideal '0' has an area of zero. In each zone, the controller makes a decision on whether a '0' or '1' is present by comparing the actual area to some ratio of the area of an ideal '1', such as 50%. A value other than 50% could be used e.g. in the range of 30% to 70%. If the actual area is equal to or greater than this amount, it is identified as a '1'. Otherwise it is identified as a '0'. In addition, a correlation error may be obtained for each bit: for a '1', this is the difference between the area of an ideal '1' and the actual area. For a '0', the correlation error is the actual area. Thus, a code is extracted, along with a total correlation error (which is preferably the sum of the correlation errors for each bit). If the total correlation error is higher than a predetermined amount, the printer may either reject the ribbon or re-read the code and repeat the process.

A final error detection mechanism may be implemented if one of the payload bits is used for parity checking. Even parity requires an even number of '1's in the code. Odd parity requires an odd number of '1's. The parity bit is set to ensure the criterion is met, when initially generating the code prior to encoding it into the ribbon tension. Upon reading the code back, if this criterion is not met the data is identified as corrupt and discarded.

Figure 8:
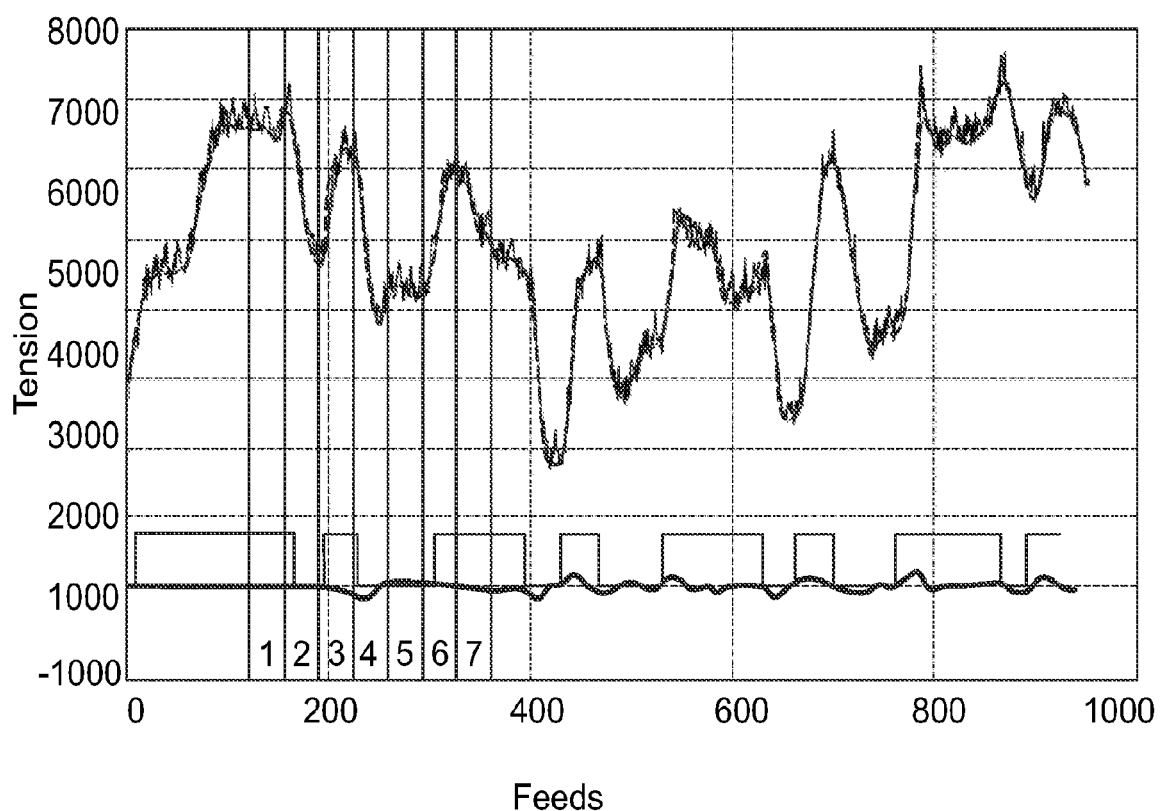
FIG. 8 is a graph showing the data from FIGS. 6 and 7 in one graph.

The entire data process algorithm is shown in FIG. 8. This diagram features a set of vertical lines which indicate the partitioning of the memory buffer into 7 zones, as numbered in FIG. 8. In addition, an ideal waveform for the code "1010011" has been overlaid. From this it can be seen how whereas zones 1 and 7 meet perfectly the criteria for a '1', zones 3 and 6 are imperfect '1's—the rising edge of the waveform begins some way into these zones, rather than at the beginning. Timing errors such as these are caused by the various noises and distortions which are present throughout the system. Similarly, zone 5 is a perfect '0' but zones 2 and 4 are imperfect '0's. Overall, the correlation error shown is FIG. 8 is sufficient such that the printer will accept the codeword as valid.

It will be appreciated that the tension code will best be encoded into the ribbon during the ribbon winding part of the ribbon manufacturing process. The tension code could be encoded at a constant linear ribbon speed or a constant ribbon rotational speed or even at a variable ribbon speed. The method described above is applicable for constant linear speed. In the case of constant rotational speed, the encoding would be modified to account for the varied linear speed. Where the algorithm depends on knowledge of the length of ribbon used to encode the tension pattern, an estimate of the length may be used rather than a precise value. The estimation of the length is based upon the diameter of the reel over the period in which the tension pattern is read back. Provided the actual length is similar to that described herein, the overall accuracy of the system should be sufficient.

Likewise it may be sufficient to implement this encoding system in only a part of the ribbon e.g. the beginning of the ribbon. This would enable each new ribbon to be identified only when first installed.

Although the above example shows the reading of an encoded ribbon in a printer including two stepper motors as drive motors, the present method can be used with a printer with a ribbon drive including one stepper and one DC motor. In such ribbon drives, the tension in the ribbon is generally controlled by using the DC motor in constant current mode to set the tension. Therefore the stepper motor does not directly measure tension or make corrections to maintain the tension within limits. In such a printer, variations in tension in the ribbon wound on the spool will result in the DC motor having to rotate slightly different amounts, compared to the stepper motor, to maintain tension. In this case, instead of the code being read by directly measuring tension, the code could be read by measuring the ratio of the length of ribbon fed by each motor. Changes in tension of the ribbon wound on the spool would produce changes in this ratio. To indirectly measure the tension, the length of ribbon fed by the DC motor may be detected by monitoring the commutation pulses produced by the DC motor; typically there are 12 commutation pulses per revolution. Alternatively, for more accuracy, an encoder could be attached to the DC motor shaft producing a higher number of pulses per revolution.

The described and illustrated embodiments are to be considered as illustrative and not restrictive in character, it being understood that only the preferred embodiments have been shown and described and that all changes and modifications that come within the scope of the inventions as defined in the claims are desired to be protected. It should be understood that while the use of words such as "preferable", "preferably", "preferred" or "more preferred" in the description suggest that a feature so described may be desirable, it may nevertheless not be necessary and embodiments lacking such a feature may be contemplated as within the scope of the invention as defined in the appended claims. In relation to the claims, it is intended that when words such as "a," "an," "at least one," or "at least one portion" are used to preface a feature there is no intention to limit the claim to only one such feature unless specifically stated to the contrary in the claim. When the language "at least a portion" and/or "a portion" is used the item can include a portion and/or the entire item unless specifically stated to the contrary.

What is claimed is:

1. A ribbon comprising:
 a substrate film, wherein the film comprises a tensionable material; and
 an ink disposed on the film;
 wherein a length of the ribbon includes portions that have been tensioned to provide a code readable from the ribbon by measuring the tension of the ribbon over the length of the ribbon.

2. The ribbon of claim 1 wherein the ribbon is between 5 and 10 micron thick.

3. The ribbon of claim 1 wherein the substrate film comprises a polyester film.

4. The ribbon of claim 1 wherein the ribbon is suitable for use with a thermal transfer printer.

5. The ribbon of claim 1 wherein the code is at least a 4 bit code.

6. The ribbon of claim 1 wherein the length of the ribbon that includes portions that have been tensioned is at least 5 m.

7. A printing system, comprising:
 the ribbon of claim 1;
 a drive mechanism for the ribbon;
 a controller; and
 a tension measurement device configured to monitor a parameter indicative of tension in the portions of the ribbon that have been tensioned to provide a code.

8. The system of claim 7 wherein the tension measurement device comprises a load cell.

9. The system of claim 7 wherein the tension measurement device comprises a moveable roller.

10. The system of claim 1 wherein the code includes information about the ribbon.

11. The system of claim 10 wherein the code includes information about the length, width, thickness, color, and/or ink type of the ribbon.

12. The system of claim 1 wherein the code includes information about operating parameters of a printer.

13. The system of claim 1 wherein the operating parameters of the printer include the maximum print speed, the nominal tension setting, and/or the heating parameters for a print head of the printer.

* * * * *